US010330595B2

(12) United States Patent
Pang et al.

(10) Patent No.: US 10,330,595 B2
(45) Date of Patent: Jun. 25, 2019

(54) OPTICAL PHASE MODULATION SYSTEMS AND METHODS

(71) Applicant: THE REGENTS OF THE UNIVERSITY OF CALIFORNIA, Oakland, CA (US)

(72) Inventors: Lin Pang, San Diego, CA (US); Yeshaiahu Fainman, San Diego, CA (US); Andrew C. Kummel, San Diego, CA (US); Brandon Hong, San Clemente, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/769,720

(22) PCT Filed: Oct. 19, 2016

(86) PCT No.: PCT/US2016/057620
§ 371 (c)(1),
(2) Date: Apr. 19, 2018

(87) PCT Pub. No.: WO2017/070159
PCT Pub. Date: Apr. 27, 2017

(65) Prior Publication Data

US 2018/0284018 A1 Oct. 4, 2018

Related U.S. Application Data

(60) Provisional application No. 62/243,556, filed on Oct. 19, 2015.

(51) Int. Cl.
*G01N 21/49* (2006.01)
*G01N 21/94* (2006.01)
(Continued)

(52) U.S. Cl.
CPC ............ *G01N 21/49* (2013.01); *G01N 15/00* (2013.01); *G01N 15/0227* (2013.01);
(Continued)

(58) Field of Classification Search
CPC .............. G01N 21/00; G01N 21/4795; G01N 21/6456; G01N 2201/0675;
(Continued)

(56) References Cited

U.S. PATENT DOCUMENTS 6,608,774 B1 * 8/2003 Rentzepis ............. B82Y 10/00 365/119
9,304,490 B2 * 4/2016 Masumura ......... G01N 21/4795
(Continued)

OTHER PUBLICATIONS

International Search Report in PCT/US16/57620, dated Jan. 24, 2017.
(Continued)

*Primary Examiner* — Sang H Nguyen
(74) *Attorney, Agent, or Firm* — Perkins Coie LLP

(57) ABSTRACT

Methods, systems, and devices for particle characterization by optical phase modulation and detection of aerosol backscattering. In some aspects, a compact and cost effective particle detector device to measure the aerosol density and its size distribution by backscattered focusing using projected optical modified field distribution imaging into the aerosol medium (air). The disclosed device can be used in a variety of scientific and industrial applications, e.g., such as a particle sensor for automobiles able to detect harmful pollution which may then be filtered from the car cabin, or warnings provided to the driver. The device can also capture and store data, enabling detailed pollution maps of various roadways in real-time.

11 Claims, 16 Drawing Sheets

(51) Int. Cl.
*G01N 21/45* (2006.01)
*G01N 15/00* (2006.01)
*G01N 15/02* (2006.01)
*G03H 1/04* (2006.01)
*G01N 15/14* (2006.01)
*G03H 1/00* (2006.01)

(52) U.S. Cl.
CPC ............. *G01N 21/45* (2013.01); *G01N 21/94* (2013.01); *G03H 1/0443* (2013.01); *G03H 1/0465* (2013.01); *G01N 2015/0046* (2013.01); *G01N 2015/0233* (2013.01); *G01N 2015/1454* (2013.01); *G03H 2001/0033* (2013.01); *G03H 2001/0447* (2013.01); *G03H 2001/0452* (2013.01); *G03H 2001/0469* (2013.01); *G03H 2222/35* (2013.01); *G03H 2222/44* (2013.01); *G03H 2225/32* (2013.01)

(58) Field of Classification Search
CPC ............ G02B 21/0032; G02B 21/0052; G02B 21/056; G02B 26/06; G03H 1/0443; G03H 2001/0458; G03H 2001/0447; G03H 2001/0083; G03H 2001/0467; G03H 2001/0072; G01B 7/00455; G01B 7/00453; G02F 1/0126
See application file for complete search history.

(56) References Cited

U.S. PATENT DOCUMENTS

| | | | |
|---|---|---|---|
| 2005/0105097 A1* | 5/2005 | Fang-Yen | G01B 9/02072 356/497 |
| 2009/0257057 A1* | 10/2009 | Novotny | B82Y 35/00 356/338 |
| 2009/0261250 A1 | 10/2009 | Zhou et al. | |
| 2011/0109962 A1 | 5/2011 | Cui et al. | |
| 2011/0122416 A1* | 5/2011 | Yang | A61B 5/0059 356/457 |
| 2012/0182561 A1* | 7/2012 | Masumura | A61B 5/0095 356/601 |
| 2012/0182591 A1* | 7/2012 | Masumura | G01N 21/00 359/11 |
| 2012/0327287 A1* | 12/2012 | Meyers | G01B 11/24 348/335 |
| 2013/0206963 A1 | 8/2013 | Grund | |
| 2013/0222786 A1 | 8/2013 | Hanson et al. | |
| 2014/0303463 A1* | 10/2014 | Robinson | A61B 5/14552 600/316 |
| 2016/0011564 A1* | 1/2016 | Tanabe | G02F 1/13471 359/11 |
| 2016/0086681 A1* | 3/2016 | Leung | G21K 1/06 378/84 |
| 2016/0291137 A1* | 10/2016 | Sakimura | G01S 17/58 |

OTHER PUBLICATIONS

Doherty et al., "Measurement of the lidar ratio for atmospheric aerosols with a 180 degree backscatter nephelometer", App. Opt. 38, 1823 (1999).
Gao et al., "Measurement of aerosol number size distributions in the Yangtze River delta in China: Formation and growth of particles under polluted conditions", Atmos. Environ. 43, 829-836 (2009).
Slezakova et al., "Atmospheric nanoparticles and thiri impadts on public health", INTECH, 2013. http://dx.doi.org/10.572/54775.

* cited by examiner

OPTICAL PHASE MODULATION SYSTEMS AND METHODS

CROSS-REFERENCE TO RELATED APPLICATIONS

This patent document claims the benefit and priority of U.S. Provisional Patent Application No. 62/243,556 entitled "OPTICAL PHASE MODULATION SYSTEMS AND METHODS" filed on Oct. 19, 2015. The entire content of the aforementioned patent application is incorporated by reference as part of the disclosure of this patent document.

TECHNICAL FIELD

This patent document relates to systems, devices, and processes for optical phase modulation by detecting aerosol backscattering.

BACKGROUND

Air pollution is the existence of particulates, molecules, or other harmful materials into the atmosphere. Air pollution is considered to be a growing global problem, which is known to cause disease, death, or damage to living organisms including animals and plants.

SUMMARY

Disclosed are systems, devices, and methods for particle characterization by optical phase modulation and detection of aerosol backscattering. In some aspects, a compact and cost effective particle detector device to measure the aerosol density and its size distribution by backscattered focusing using projected optical modified field distribution imaging into the aerosol medium (air). The disclosed device can be used in a variety of scientific and industrial applications, e.g., such as a particle sensor for automobiles able to detect harmful pollution which may then be filtered from the car cabin, or warnings provided to the driver. The device can also capture and store data, enabling detailed pollution maps of various roadways in real-time.

The subject matter described in this patent document can be implemented in specific ways that provide one or more of the following features. For example, the disclosed technology includes techniques using optical phase pattern to generate optical field distribution in an aerosol medium, enhance the backscattered or forward scattered signal by backscattering or forward scattered focusing, and distinguish the aerosol size distribution by projecting the selected sizes of the optical phase patterns. For example, the disclosed technology can utilize both optical power and optical phase to enhance the optical power needed to detect the backscattered or forward scattered signal. For example, the disclosed technology can achieve compact back scattering detection, e.g., capable for mobile device platform or other compact devices. For example, the disclosed technology can provide an aerosol size distribution directly.

BRIEF DESCRIPTION OF THE DRAWINGS

FIG. 1A shows an illustrative diagram of an example optical phase modulation system of the present technology.

FIG. 1B shows a block diagram of an example embodiment of a data processing unit of the optical phase modulation system.

FIG. 2 shows an illustration of an example zone plate.

FIG. 3 shows a plot of the field distribution of the projected phase pattern generated on SLM and the designed field distribution.

FIG. 4 shows a plot of the field distribution of the electric field after the zone plate like field reflected from the mirror located at the right boundary.

FIG. 5 shows a plot of back scattered focusing by a layer of randomized aerosols.

FIG. 6 shows a plot of significantly weakened back scattered focusing by a layer of randomized aerosols.

FIGS. 7A and 7B show data plots of the scattering characterization of single particle 800 nm in diameter from COMSOL in angular spectra and field distribution.

FIGS. 8A and 8B show plot of back scattering focusing of aerosol medium without and with projected zone plate field distribution.

FIG. 9 shows a plot of an electric field magnitude of the back scattering of aerosol medium with area density $30/mm^2$.

FIG. 10 shows a plot of an electric field magnitude of the back scattering of aerosol medium with area density $10/mm^2$.

FIG. 11 shows a plot of an electric field magnitude of the back scattering of aerosol medium with area density $6/mm^2$.

FIG. 12 shows a plot of an electric field magnitude of the back scattering of aerosol medium with area density $3/mm^2$.

FIG. 13 shows a data plot depicting the aerosol density distribution versus the aerosol size.

FIG. 14 shows an illustration of forward scattered focusing.

FIG. 15 shows a plot of a simulated forward and back scattered focusing by two layers of random distributed ware particles.

FIG. 16 is a flowchart representation of an example method for characterizing particulates in an aerosol medium.

DETAILED DESCRIPTION

With the increase of human activities, air pollution becomes huge issue. Although many measures have been taken to increase the efficiency of cars, employment of advanced technologies to reduce emission and development of green energy farms to replace power plants, air pollution in developed counties and developing counties is common. Epidemiological studies show the health effects of atmospheric aerosols, respiratory irritation and changes in pulmonary function. Some studies have suggested that smaller particles could cause severe damage to the lung. Smaller particles can penetrate alveolar epithelium, enter the pulmonary interstitial and vascular space into blood stream. Acquiring the size distribution of atmospheric aerosols, together with its density, not only provides important information on the level of the air quality, but also the sources of the particles. According to Mie scattering theory, if the incident intensity of the optical beam is 1 $w/m^2$, at the distance of 0.1 m, the forward scattered intensity by a particle of 10 microns is about $10^{-6}$ $w/m^2$, while the back scattered intensity is $10^{-11}$ $w/m^2$. When the size of the particle reduces to 100 nm, the back scattered intensity becomes 4 orders smaller, $10^{-15}$ $w/m^2$. Therefore, current techniques for detecting the particles either employ an air chamber to pass aerosols into laser beam or electric field to acquire the information of the size and the density, or use high power laser to acquire backscattering signal from the particles. Bulky, air chamber or high power in current approaches are the direct consequence of the weak scattered signal.

Disclosed are systems, devices, and methods for characterization of particles in an aerosol medium by optical phase modulation and the detection of aerosol backscattering. In some aspects, a compact and cost effective particle detector device to measure the aerosol density and its size distribution by backscattered focusing using projected optical modified field distribution imaging into the aerosol medium (air). The disclosed device can be used in a variety of scientific and industrial applications, e.g., such as a particle sensor for automobiles able to detect harmful pollution which may then be filtered from the car cabin, or warnings provided to the driver. The device can also capture and store data, enabling detailed pollution maps of various roadways in real-time by integrated data form sensors in multiple car along the highway system.

The disclosed technology provides a compact detection platform, e.g., instead of laser beam, using light with a spatially modulated optical field as illumination, such that the illuminated aerosols scatter the light with certain optical pattern; interference among the all the scattered signals form a concentrated spot (e.g., called back scattered focusing) at the designated detector position to enhance the back scattered signal. The enhanced back scattered light can be further amplified by interference with the built-in reference beam to realize the heterodyne or homodyne amplified detection. Employing the same concept, forward focusing modulation can also be implemented to enhance the forward scattering signal.

FIG. 1A shows an illustrative diagram of an example optical phase modulation system 100 of the present technology operable for backscattered focusing and homodyne (heterodyne) detection (forward scattered focusing can also be formed). The system includes a light source 2 to emit a light beam into an optical circuit, which includes beam splitters 3 and 4, mirrors 5 and 14, wave plates (e.g., half wave plate 6, quarter wave plate 8), polarization dependent beam splitter 7, spatial light modulator 9 and optical phase passes beam splitter 10, and lens 11, to split the light beam into a signal beam and a reference beam and manipulate the beams for projection into an aerosol medium such that the backscattering patterns are detected at optical detector 1.

Implementations of the system 100 can include the following example. The light (e.g., laser beam) from the light source 2 (e.g., laser) is divided into two beams after passing the beam splitter 3. The two beams are called reference beam and signal beam, respectively. The reference beam is directly reflected by the beam splitter 3 and reflected back by the mirror 5, re-directed by the splitter 4, passing through the beam splitter 3, enters the detector 1, where it interferes with the signal beam back from the aerosol scattering.

The signal beam passes a half wave plate 6, polarization dependent beam splitter 7 and quarter wave plate 8, then reflects at the surface of the spatial light modulator (SLM) 9, which can modify the optical phase of the reflected light. The reflected signal beam with modified optical phase passes beam splitter 10, and projected by the lens 11 into the aerosol medium 12 and forms the field distribution pattern 13. The projected optical pattern illuminates the aerosol medium in such way that the back scattered light from different parts add together in phase (constructively), or interferes. Therefore, the backscattered light is enhanced. The enhanced back scattered light can be further amplified by homodyne or heterodyne detection by interfering the back scattered light with reference beam at the detector 1.

FIG. 1B shows a block diagram of an example embodiment of the data processing unit of the system 100. In this example, the data processing unit include a processor to process data and a memory in communication with the processor to store data. For example, the processor can include a central processing unit (CPU) or a microcontroller unit (MCU). For example, the memory can include processor-executable code, which when executed by the processor, configures the data processing unit to perform various operations, such as receiving information, commands, and/or data, processing information and data, and transmitting or providing information/data to another entity (e.g., external device). To support various functions of the data processing unit, the memory can store other information and data, such as instructions, software, values, images, and other data processed or referenced by the processor. Various types of Random Access Memory (RAM) devices, Read Only Memory (ROM) devices, Flash Memory devices, and other suitable storage media can be used to implement storage functions of the memory. The memory can store data and information of the data processing unit and other units of the system. For example, the memory can store system unit parameters, and hardware constraints, as well as software parameters and programs for operation on the system. In this example, the data processing unit includes an I/O unit that can allow communicative connectability of the data processing unit to other units of the system. For example, I/O unit can provide the data processing unit to be in communications with other devices or systems, e.g., by using various types of wired or wireless interfaces compatible with typical data communication standards, for example, including, but not limited to, Universal Serial Bus (USB), IEEE 1394 (FireWire), Bluetooth, Bluetooth Low Energy (BLE), Zig-Bee, IEEE 802.11 (Wi-Fi), Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. The I/O unit can also provide communicative connectability of the data processing unit to an external interface, a source of data storage, or a display device. The I/O unit of the data processing unit can also interface with other external interfaces, sources of data storage, and/or visual or audio display devices, etc. to retrieve and transfer data and information that can be processed by the processor, stored in the memory, or exhibited on an output unit of the system.

The disclosed technology provides techniques that include projecting the phase pattern generated at SLM into the aerosol medium or air and forms the designed electric field distribution in air or in aerosol medium. Illuminated aerosols in the projected patterns scatter the light backward; the backscattered light from different parts of the projected pattern interfere coherently and form a focus at the designed spot for detection. Forward scattered focusing can also be formed because of the same principle.

The disclosed systems can be implemented to measure the aerosol density and its size distribution by backscattered focusing using projected programmable (see section on SLM) optical modified field distribution imaging into the aerosol medium (air). The projected optical field distribution by the optical phase modulation modifies the optical phase of the back scattered light from aerosols; the backscattered light from the different patterns of the projected optical field interferes constructively and form a concentrated optical spot at the detector, enhancing the backscattering signal significantly. The projected optical field distribution pattern can be adjusted to form backscattered focusing for different sizes of aerosol, detecting the aerosol size distribution. The forward scattering from the particles by the projected field pattern can also be affected to form forward scattered focusing to enhance the forward scattering signal. Forward scattered focusing can also be used to evaluate the aerosol sizes (using a programmable phase plate; see section on SLM) and their distributions.

I. The Projected Phase Distribution into the Air Forms Designed Electric Field Distribution As an example, a Zone Plate Pattern was used as the projected field distribution formed in the air (or aerosol medium).

A zone plate (e.g., Fresnel zone plate) is a device used to focus light passing it or form an image. Zone plates use diffraction instead of refraction or reflection. A zone plate consists of a set of radially symmetric rings, known as Fresnel zones, which alternate between opaque and transparent. Light hitting the zone plate will diffract. The zones can be spaced so that the diffracted light constructively interferes at the desired focus, creating an image there.

To get constructive interference at the focus, the zones should switch from opaque to transparent at radii, as shown in FIG. 2. FIG. 2 shows an illustration of an example zone plate. On the left of FIG. 2, the illustration shows the amplitude zone plate with transparent and opaque zones. On the right of FIG. 2, the illustration shows the side view of the field pattern.

The ring radii are described in Equation (1):

$$r_n = \sqrt{n\lambda f + \frac{n^2\lambda^2}{4}} \quad (1)$$

where n is an integer, λ is the wavelength of the light the zone plate is meant to focus and f is the focal length, defined by the distance from the center of the zone plate to the focus.

The maximum possible resolution of a zone plate depends on the smallest zone width. Therefore, the smallest size object we can image, smallest spot we can focus, is limited by how small you can reliably make the zones.

First, the zone plate is projected as an optical field distribution in air (into the aerosol medium). In order to do this, we modify the surface of the SLM by varying the positions of each pixel on SLM, and check the field distribution in air. FIG. 3 shows one example of the projected field distribution. Green line corresponds the designed zone plate like field distribution in air, blue line corresponds to the actually imaged (projected) in the air. We can see that the projected field form approximates the profile of the zone plate like electric field distribution; in reality, illuminated and non-illuminated areas although the field along the illuminated areas are not completely uniform as designed. The fields in the non-illuminated areas are nonzero, a non-ideality as a byproduct of the scattering process.

FIG. 3 shows a plot of the field distribution of the projected phase pattern generated by SLM (blue line 302) at the image plane. The green line 304 shows the designed field distribution. Vertical axis is the electric field (relative values), the horizontal axis is the position (in microns). The plot of FIG. 3 shows the comparison of the designed (green line 304) and actual (blue line 302) field distribution generated by a projected phase pattern, which demonstrates the zone plate like field distribution can be formed in air or aerosol medium to illuminate the aerosols with varied optical fields.

For clarification, the phase pattern at SLM is calculated by inverse optimization. By inputting the required field distribution design, the projected field distribution is calculated. Optimization is taken by comparing the calculated field with required design or the previously calculated field distribution; reiteration is set to end till the error is within the reasonable value.

FIG. 4 shows a plot of the field distribution of the electric field after the zone plate like field reflected from the mirror located at the right boundary. The color bar 402 shows the relative field magnitude.

II. The Projected Zone Plate Like Field Distribution Can Form Back Reflected Focusing It is known that light passing a physical formed zone plate can focus; however, it should be shown that the projected zone plate formed in air (e.g., as shown in FIG. 3) can concentrate light. To demonstrate this, we modeled placement of a reflector at the position where the zone plate field distribution is formed to see if there is back reflected focal point generated by the interference of the light reflected from the zone plate (shown in FIG. 4). The designed (projected) zone plate has focal length of 70 microns with total size of 40 microns in diameter and minimal width of 1 micron. In FIG. 4, we observe the back reflected focusing from the zone plate. The focal length (from the zone plate distribution or the right boundary where the reflector is located to focal point) is indeed 70 microns, which is the exact value of the designed value.

III. The Projected Zone Plate Like Field Distribution into Aerosol Medium Forms Back Scattered Focusing We use COMSOL (COMSOL Multiphysics®) to simulate the projected phase distribution into aerosol medium. We put one layer of aerosol (water particles) at the position of the zone plate like field distribution. The particles with 400 nm in diameters are randomly distributed in the line (shown in FIG. 5) at 50 microns. The designed focal length of the zone plate is 70 microns with minimal zone width of 1 micron. As shown in FIG. 5, we see a focused point is formed by the backscattered light from the aerosols. There is no back scattered focusing formed when there are no aerosols. The formed focal length (from the line of the aerosols to the focal point) is 70 microns, matching the designed value.

FIG. 5 shows a data plot of back scattered focusing by a layer of randomized aerosols. The field distribution of the electric field is scattered field by the aerosols. The color bar shows the field magnitude.

IV. The Size Dependence of the Back Scattered Focusing from the Projected Zone Plate Like Field Distribution Keeping the parameters in the above-mentioned zone plate distribution the same, changing the diameter of the aerosols to 800 nm, we calculate the back scattering field shown in FIG. 6. We can see that the back scattered focusing is significantly dampened, becoming difficult to detect. The result shows that applying a single zone plate projection to different aerosol sizes is not optimized for maximal backscattering efficiency. Based on the Mie theory, the particle with 800 nm in diameter gives one order higher back scattered intensity than that of 400 nm. However, the result shown in FIG. 6 tells us that one order higher signal does not contribute into the back scattered focusing. The outermost zone width in zone plate field distribution used in above calculation is about 1.2 microns. On an average, about 3 particles with 400 nm in diameter could dwell in the radial line in the outermost zone, while only one 800 nm particle could reside. Generally, the outermost zone could house $10^5$ particles with 400 nm in diameter, but $10^4$ particles with 800 nm in diameter instead. The inner zones would give even higher housed particle number difference. Therefore, by modifying the sizes of the zone plate, monitoring backscattered focusing, the size distribution in the aerosol could be determined.

FIG. 6 shows a data plot of significantly weakened back scattered focusing by a layer of randomized aerosols. The field distribution of the electric field is scattered field by the aerosols. The color bar 602 shows the field magnitude.

V. Green's Function Calculation

The calculation or simulation of full aerosol medium could not be conducted by the commercially available software due to required computing power. Instead, a Green's function like approach was employed for the calculation.

1. The scattering field of a single particle was calculated, assuming incident field as unity, as shown in FIGS. 7A and 7B, which shows the field (angular) distribution of single particle scattering using COMSOL (this can be also done by using theoretical analysis for regular (sphere) particle using Mie theory). We define the field distribution by single particle as $E_p(x,y)$. FIGS. 7A and 7B show data plots of the scattering characterization of single particle 800 nm in diameter from COMSOL in angular scattering magnitude (FIG. 7A) and cross-sectional field distribution (FIG. 7B).

2. Matlab was used to acquire the designed field distribution of the projected zone plate, defined as $E_{ph}(x,y)$, a weighting transparency function.

3. The scatterers (particles) are placed in the field generated by the zone plate, or randomize the positions of the particles in the medium into the field distribution.

4. The scattering field of one scatterer (particle) under the illumination of the projected field is $E_s = E_p \times E_{ph}$.

5. The total scattering field is the superposition of each particle:

$$S = \sum_i E_{s_i} = \sum_i E_{ph} \cdot E_{p_i}$$

Applying the above approach to a big size zone plate (5 cm in outer zone, and 50 m focal length), we estimate the efficacy of the Green's function. As shown in FIG. 8A and FIG. 8B, the proposed approach works successfully. As aerosols exist randomly in the whole space, the projected zone plate like field distribution indeed forms the back scattered focusing at the designed focal spot. The back scattered focusing disappears when the projected zone plate is taken away.

FIGS. 8A and 8B show plot of back scattering focusing of aerosol medium without (FIG. 8A) and with (FIG. 8B) projected zone plate field distribution.

VI. Efficiency Estimation

With the established Green's function approach, we estimate the efficiency of the back scattered focusing. The efficiency is defined as the ratio of reflected power at the back scattering focal point to the incident power (only calculated the field at the focal point; for practical application, integration over the detector area should be conducted). Natural to two dimensional simulation, the density of the aerosol is described as the area density, or number of particles in one millimeter square.

First example: the size of the projected zone plate is 0.9 cm with the focal length of 1 m. The aerosol medium consists of particles of 800 nm in diameter. The illumination wavelength is 600 nm. The back scattered focusing by particle density of 30/mm² is shown in FIG. 9, which shows the efficiency of $\eta \approx 1.6 \times 10^{-11}$. When the density is reduced to 10/mm², the efficiency is reduced to $\eta \approx 2 \times 10^{-12}$ as shown in FIG. 10, where the projected zone plate is of the same parameters as used in FIG. 9.

FIG. 9 shows a plot of an electric field magnitude of the back scattering of aerosol medium with area density 30/mm². The curve 902 shows results with DOE. No back scattered focusing is also shown of the case without projected zone plate generated by diffracted optical element (labeled as 'no DOE' 904).

FIG. 10 shows a plot of an electric field magnitude of the back scattering of aerosol medium with area density 10/mm² (curve 1002). No back scattered focusing is also shown of the case without projected zone plate (labeled as 'no DOE' 1004).

When the particle density further reduces to 6/mm², using the same projected zone plate, no back scattered focusing is formed as shown in FIG. 11. The curve 1102 shows results with DOE and curve 1104 shows results with No DOE.

When we change the parameters of the projected zone plate. The size of the projected zone plate is 5 cm with the focal length of 50 m. The aerosol medium is kept the same, or particles of 800 nm in diameter. The illumination wavelength is 600 nm. The density is set to 7/mm², back scattering is formed and the efficiency is $1 \times 10^{-14}$. Further reducing the density to 3/mm², back scattering focusing is still formed, the efficiency is $2.3 \times 10^{-15}$.

By optimizing the zone plate, embodiments can achieve higher efficiency, or back scattered focusing, for a given lower particle area density.

VII. Feasibility for Real Environmental Applications

The calculations above shows that the back scattered focusing forms at the density of more than 3/mm². The optimized design and homodyne or heterodyne detection would reduce the detectable density even lower. In the real environment, the density varies responding to the location (near emission sources: power plants, roads) and time period (for example, traffic hours etc.).

Figure 13:
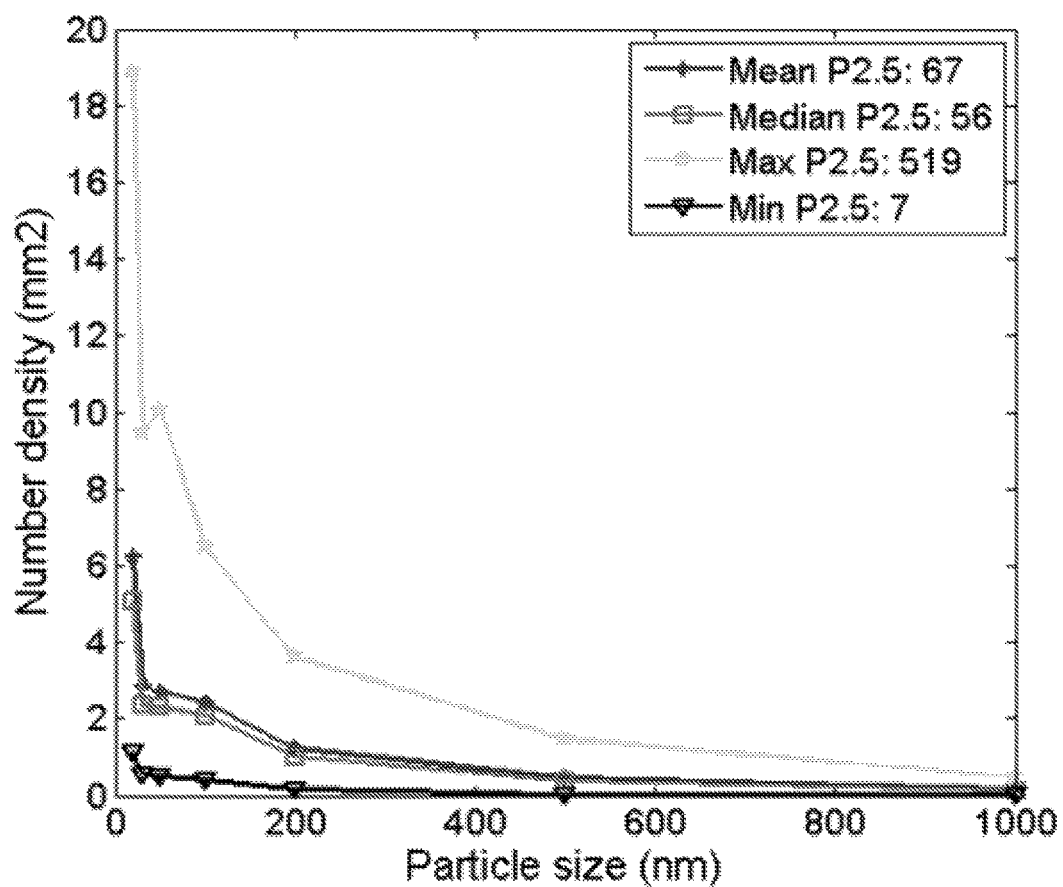

FIG. 13 shows a data plot depicting the aerosol density distribution versus the aerosol size, showing a typical particle number density during May 2 to Jun. 2, 2005, at a town in Yangtze Delta area, a population of over 100 million, 45 km northwest of home to China's largest city, Shanghai, a major industrial and commercial hub in China (Gao, 2009). FIG. 13 shows the maximal, minimal, mean and median distribution of the particle density measured during one month period. The area densities are calculated from the volume densities monitored in site. In the legend, also gives the measured PM2.5.

Particulate matter (PM) is microscopic solid or liquid matter suspended in the Earth's atmosphere. PM2.5 refers to the suspended matters in diameter of 2.5 microns or less; the unit is microgram per meter cube. Due to the highly toxic health effects of particulate matter, most governments have created regulations both for the emission allowed from certain types of pollution source (e.g., motor vehicles, industrial emissions etc.) and for the ambient concentration of particulates. Table 1 lists the air quality standards regulated by selected counties.

TABLE 1

Air quality standards for atmosoheric particles in selected countries*

| Country | Pollutant | Yearly average | Daily average |
|---|---|---|---|
| European Union | PM2.5 | 25 ($\mu$g/m$^3$) | / |
| USA | PM2.5 | 15 ($\mu$g/m$^3$) | 35 ($\mu$g/m$^3$) |
| Canada | PM2.5 | 30 ($\mu$g/m$^3$) | 30 ($\mu$g/m$^3$) |
| Australia | PM2.5 | 8 ($\mu$g/m$^3$) | 25 ($\mu$g/m$^3$) |
| Japan | PM2.5 | 15 ($\mu$g/m$^3$) | 35 ($\mu$g/m$^3$) |
| China | PM2.5 | 35 ($\mu$g/m$^3$) | 75 ($\mu$g/m$^3$) |

*The data may have been changed due to stricter requirements. (Slezakova, 2013)

As shown in FIG. 13, the heavily polluted period (PM2.5 is about 519 in maximal cases) corresponds to the area density of 19, far higher than the detectable density of 3/mm$^2$ by the proposed approach, in both forward and back scattered focusing. The area density in median cases of PM2.5 of 56 is about 5/mm$^2$, still in the detectable range. It indicates that the disclosed back scattered focusing is suitable for the employment in the polluted fields. Using the enhanced methods, this approach could even be used in the clear air environment, which is below the states' regulation values.

Figure 14:
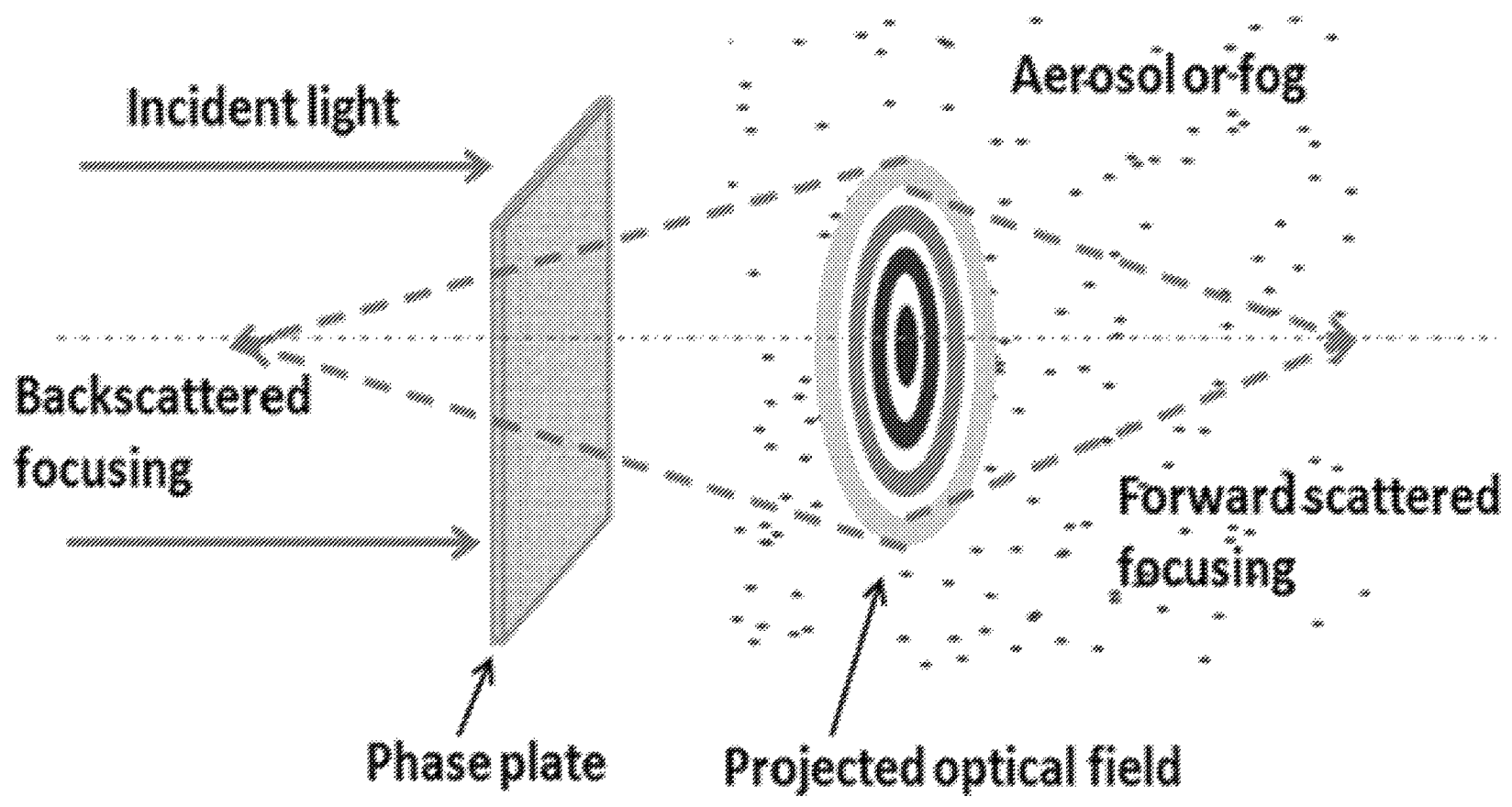

VIII. Forward Scattered Focusing by Zone Plate Like Field Distribution in Aerosol Medium Particles scatter the light into all the directions. According to Mie theory, the particles usually scatter more light into forward direction (along the light propagating direction). Now that projected zone plate can form back scattered focusing, it can also form forward scattered focusing, which could be used to enhance the forward scattering signal. The principle of forward scattered focusing is illustrated in FIG. 14. A phase distribution device is projected into the aerosol medium by the incident light; a zone plate like field distribution is formed in the medium. The particles in the zones scatter the light into all directions. Besides the back scatter direction (as we demonstrate in previous sections), in forward direction, the scattered light in different zones are in phase, therefore, interfere constructively.

Figure 15:
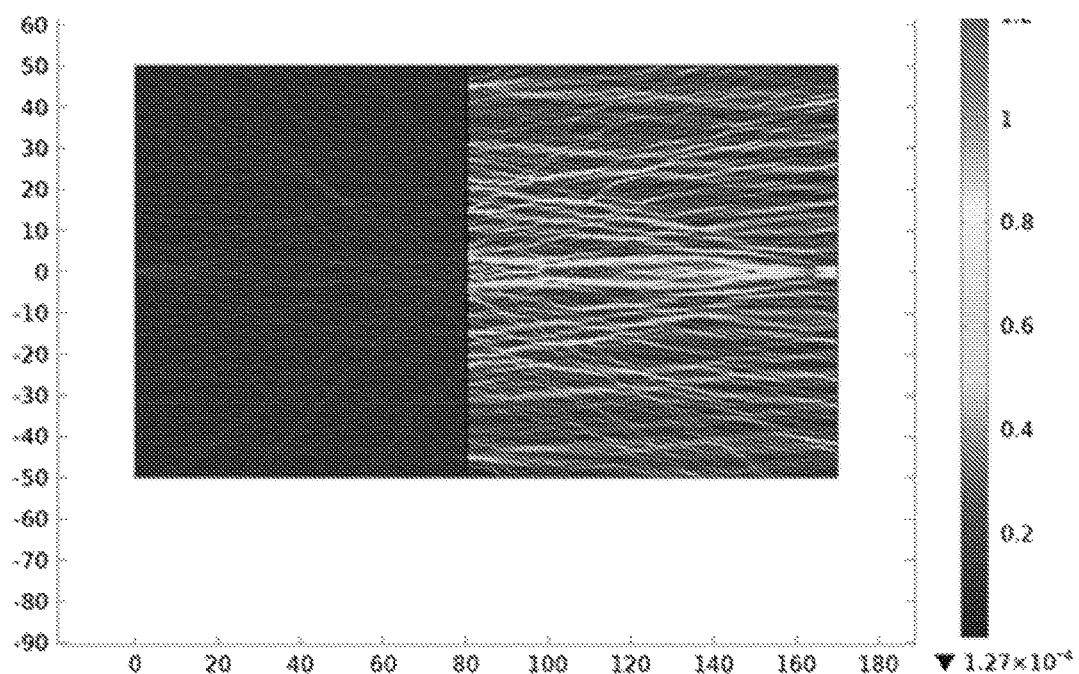

FIG. 15 shows the simulated forward and back scattered focusing formed by the randomly distributed particles in one layer. The maximum field in the front (forward) and back (backward) focal planes are 1.32 and 0.27V/m, respectively, when incident light is set to 1V/m. Therefore, the estimated efficiency for forward scatted focusing is about 25 times compared to back scattered focusing. The designed diffractive optical device (DOE) is about 100 µm in diameter; focal length of the projected Fresnel zone pattern is about 80 µm; the illumination wavelength is 600 nm; the diameter of particles is 200 nm.

Example Embodiments and Implementations

Figure 1A:
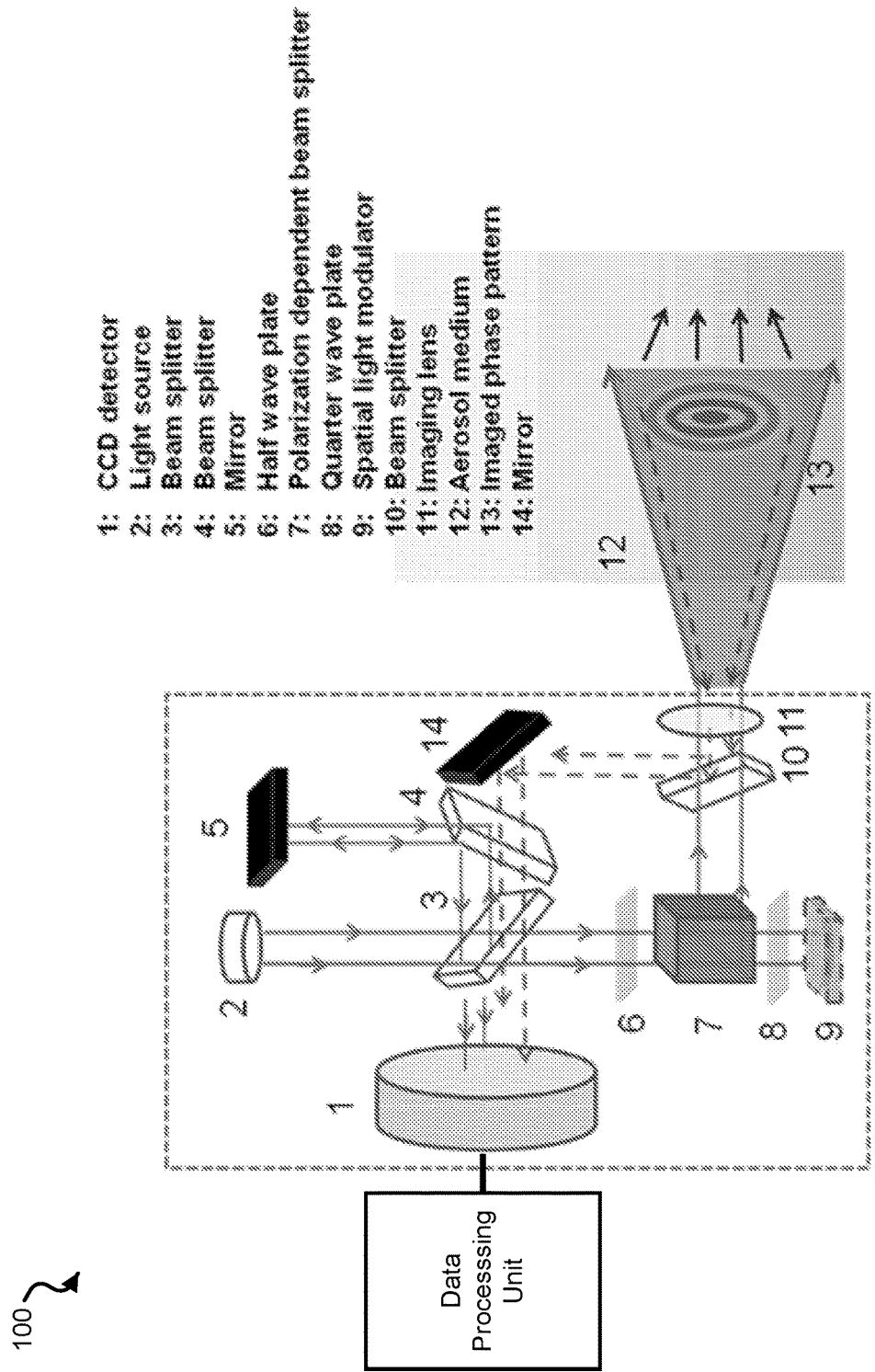

The disclosed technology can include the following example features or be implemented in the following ways, for example. In some aspects, the disclosed technology can measure the aerosol density and its size distribution by backscattered focusing using projected optical modified field distribution imaging into the aerosol medium (air). The projected optical field distribution by the optical phase modulation modifies the optical phase of the back scattered light from aerosols; the backscattered light from the different patterns of the projected optical field interferes constructively and form a concentrated optical spot at the detector, enhancing the backscattering signal significantly. The projected optical field distribution pattern can be adjusted to form backscattered focusing for different size of aerosol, detecting the aerosol size distribution. An adjustment controller may be provided to achieve the adjustment by controlling positions of the optical components (phase plate, mirror, beam splitter, etc.) using a manual or servo-controlled mechanism. The forward scattering from the particles by the projected field pattern can also be modulated to improve the focal depth of forward scattering signal propagation. Forward scattered focusing can also be used to evaluate the aerosol sizes and their distributions. In addition, the above demonstrations of the back scattered focusing by using projected zone plate patterns have thus far only considered the scattered intensity; phase information is also accessible in coherent illumination. Specifically, homodyne or heterodyne detection, which are the routings to enhance the weak signal, could be used to further amplify the back scattered signal, as shown in FIG. 1A. As shown and stated in the main text, changing the projected zone plate designs would vary the back or forward scattered intensity. In other words, optimized design of the projected zone plate like field distribution would increase the back or forward scattered focusing further. Furthermore, randomizing and algorithmically searching the SLM modulated and projected field distribution would further serve to enhance the back or forward scattered signal by changing the field distribution while in feedback, comparing the measured power at the focal point against prior projection iterations. Of course, optimization of the projected field distribution will consider the sizes of the parts of the divided fields to acquire the information of the particle size distribution. The projected field distributions would be generated by changing the phase distribution introduced by the elements of the SLM, shown in FIG. 1A.

The optical elements or devices illustrated in FIG. 1A can be integrated into a compact or on-chip platform to achieve cellphone based operation. In some implementations, for example, the disclosed technology can be configured in a mobile-based aerosol sensing device, such as on a mobile phone or communication device (e.g., smartphone, tablet, etc.) wearable communication device (e.g., smart glasses, smartwatch, etc.), integrated in a vehicle such as a car for outdoor environmental applications, or integrated in a building for indoor environmental monitoring applications.

Figure 1B:
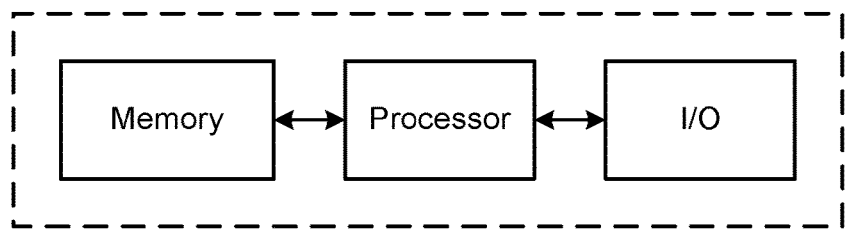
Figure 2:
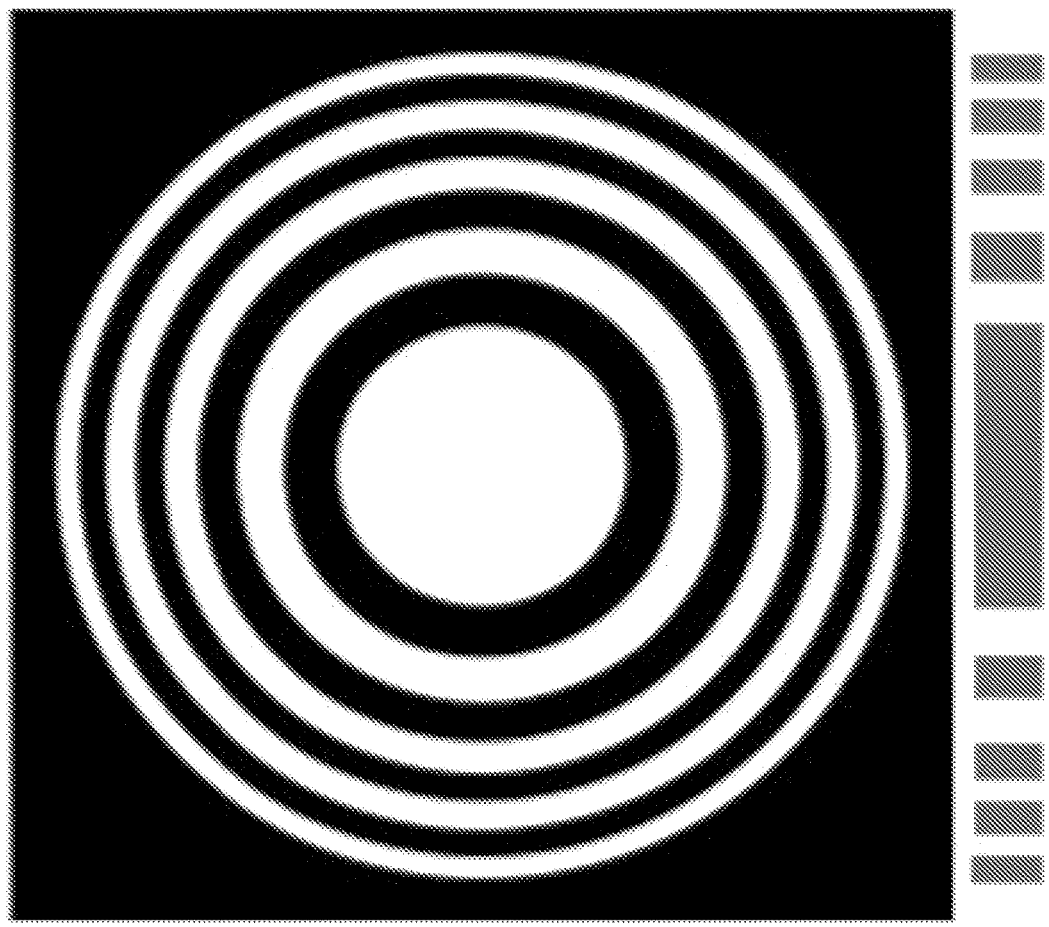
Figure 3:
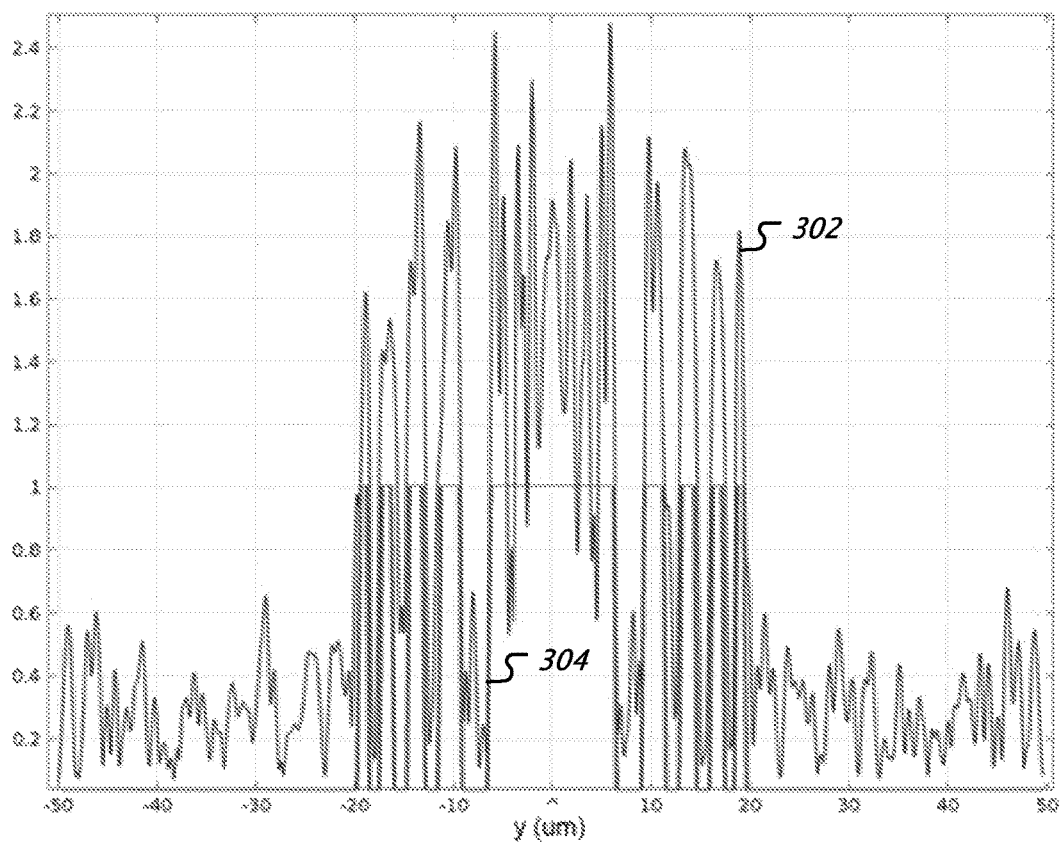
Figure 4:
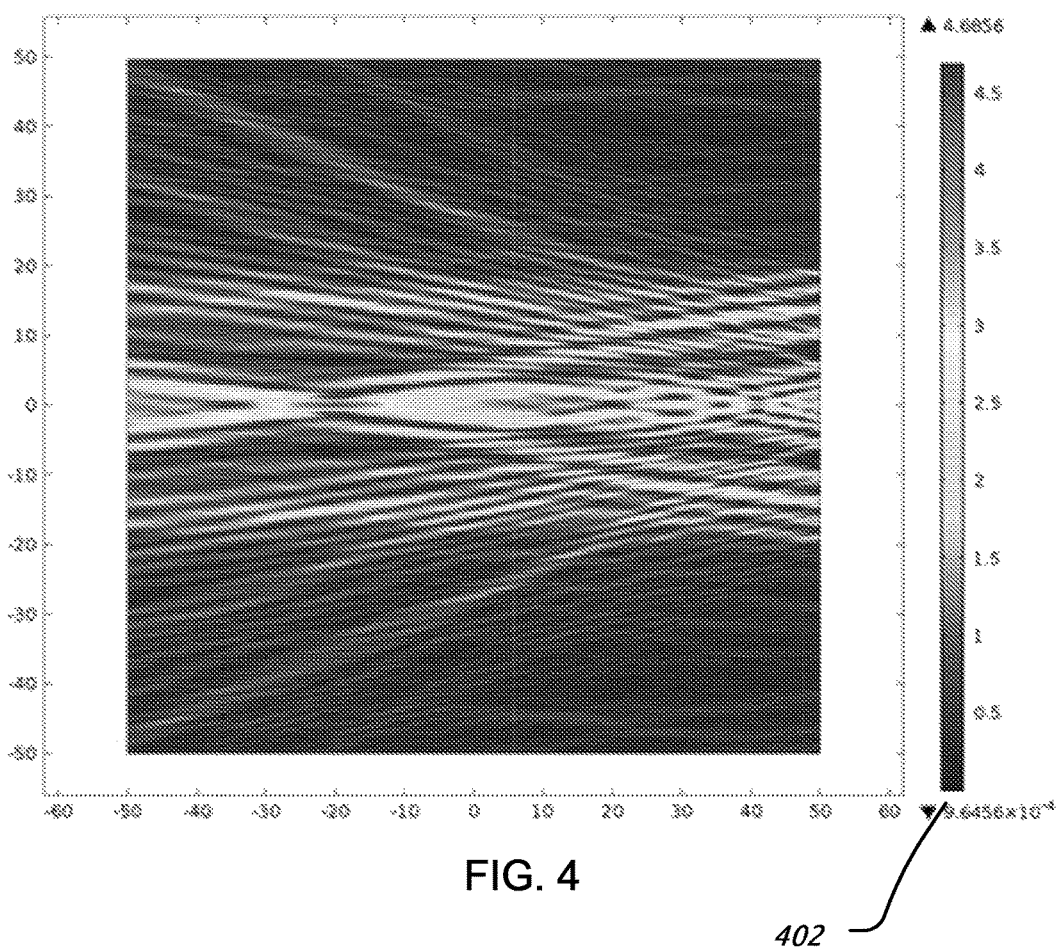
Figure 5:
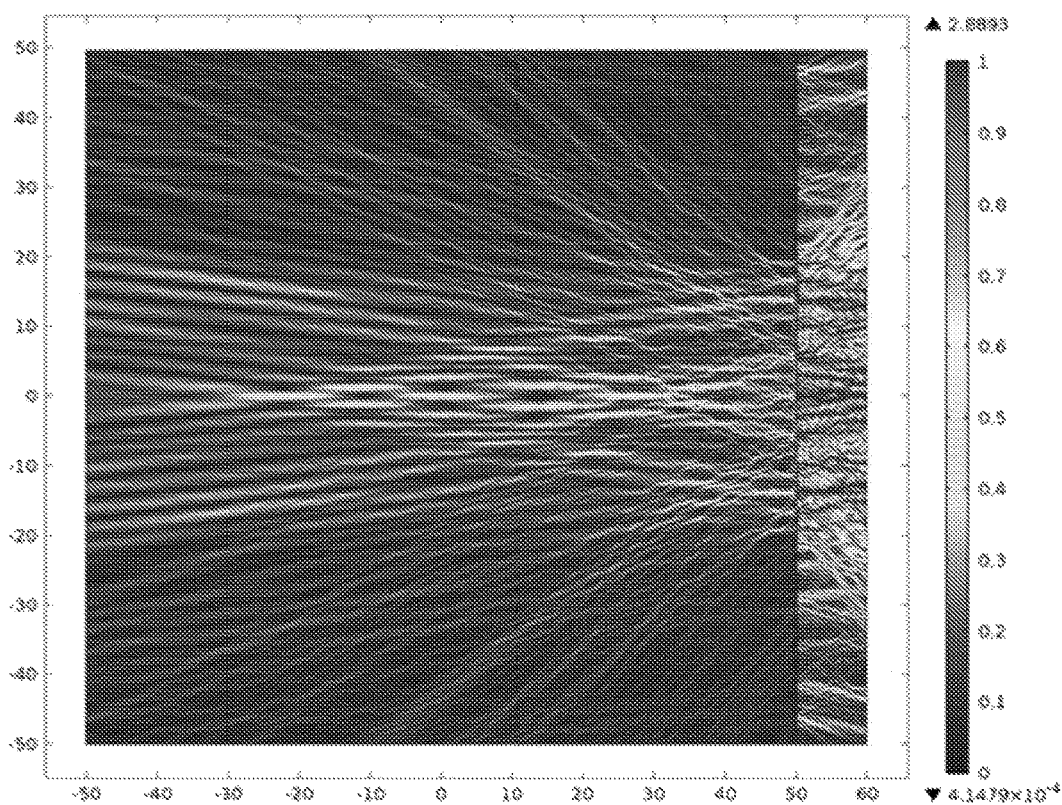
Figure 6:
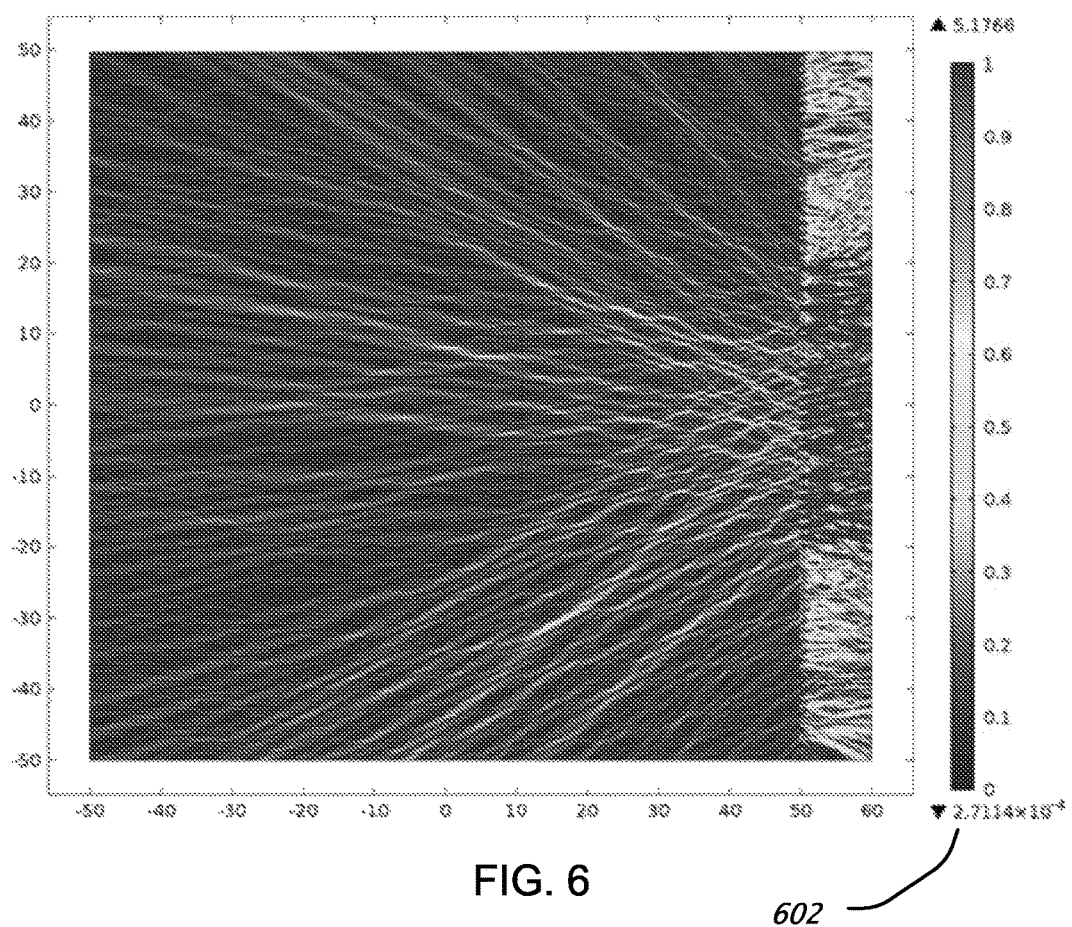
Figure 7B:
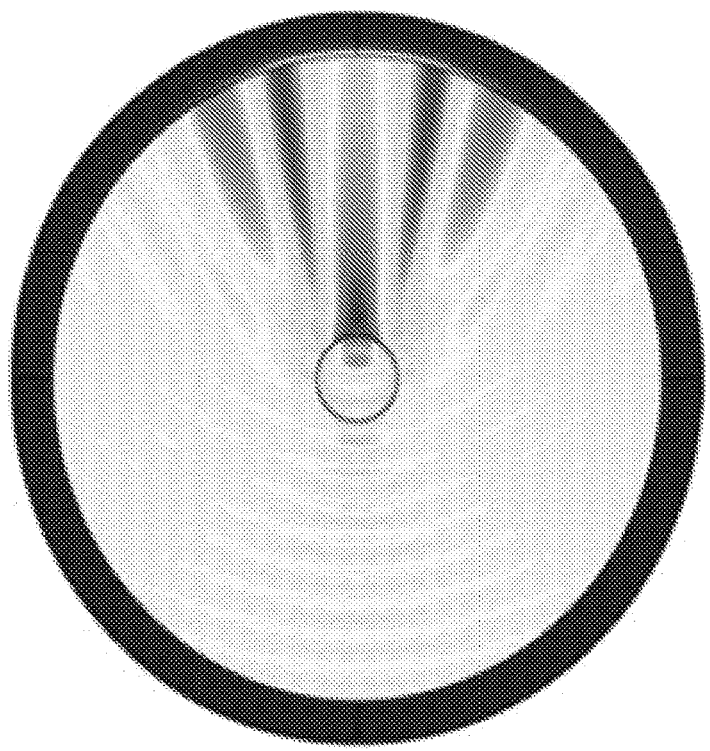
Figure 7A:
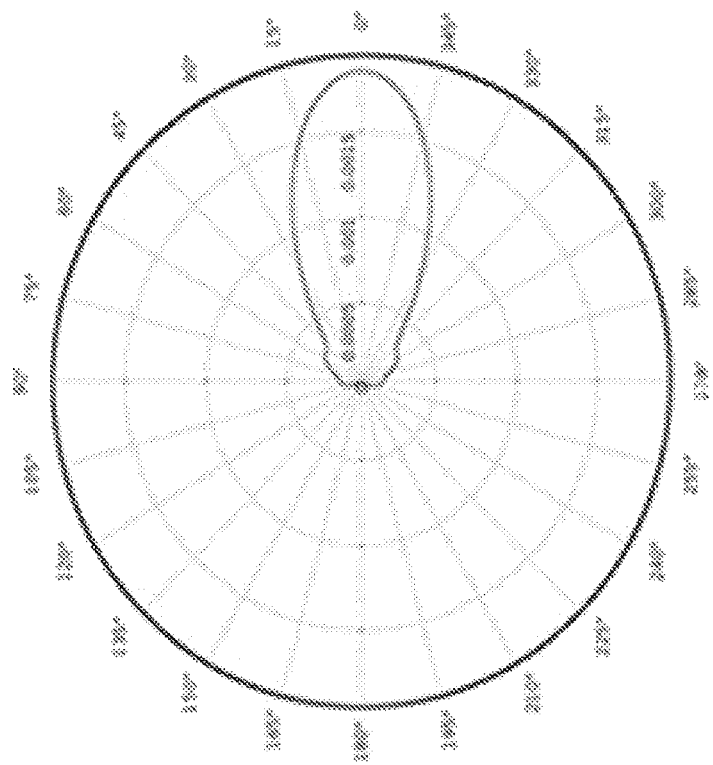
Figure 8A:
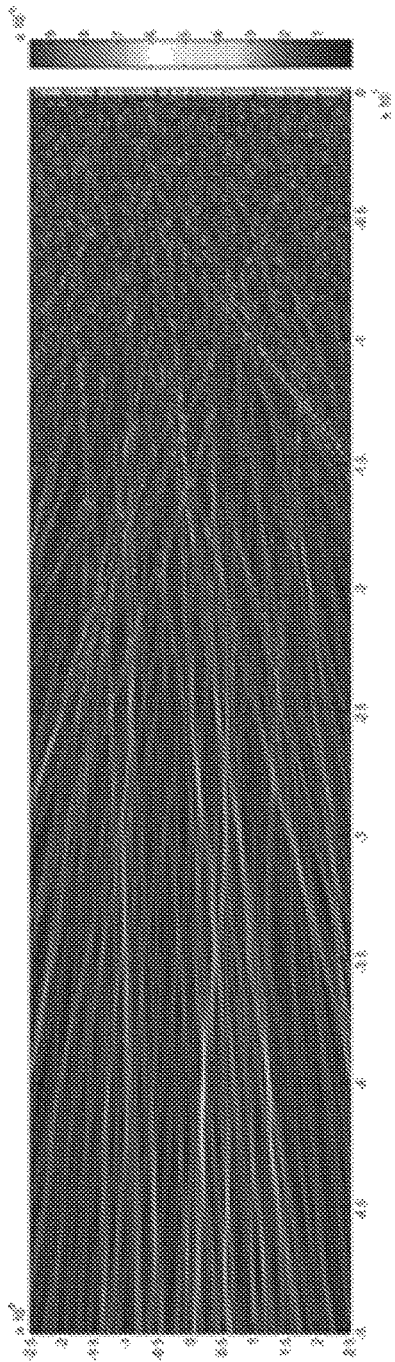
Figure 8B:
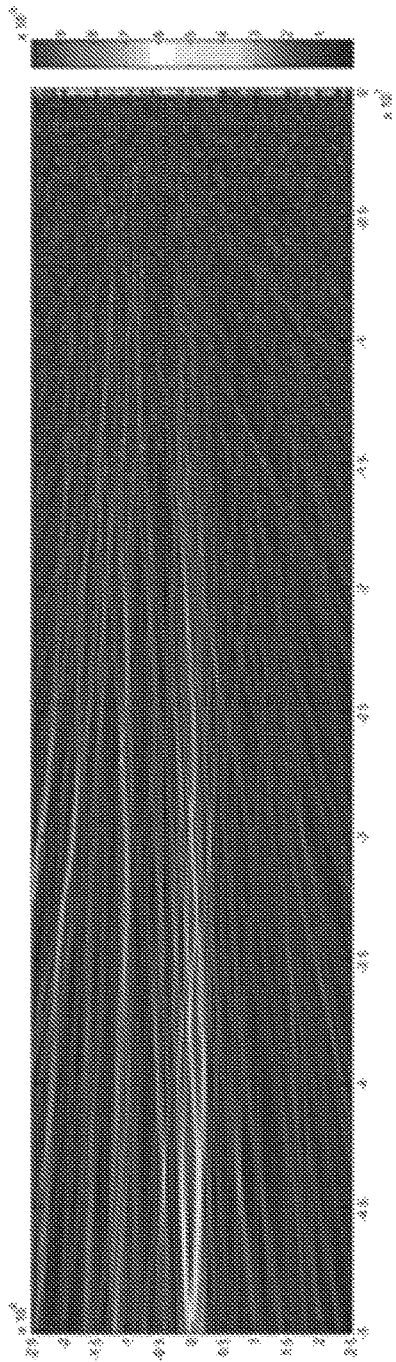
Figure 9:
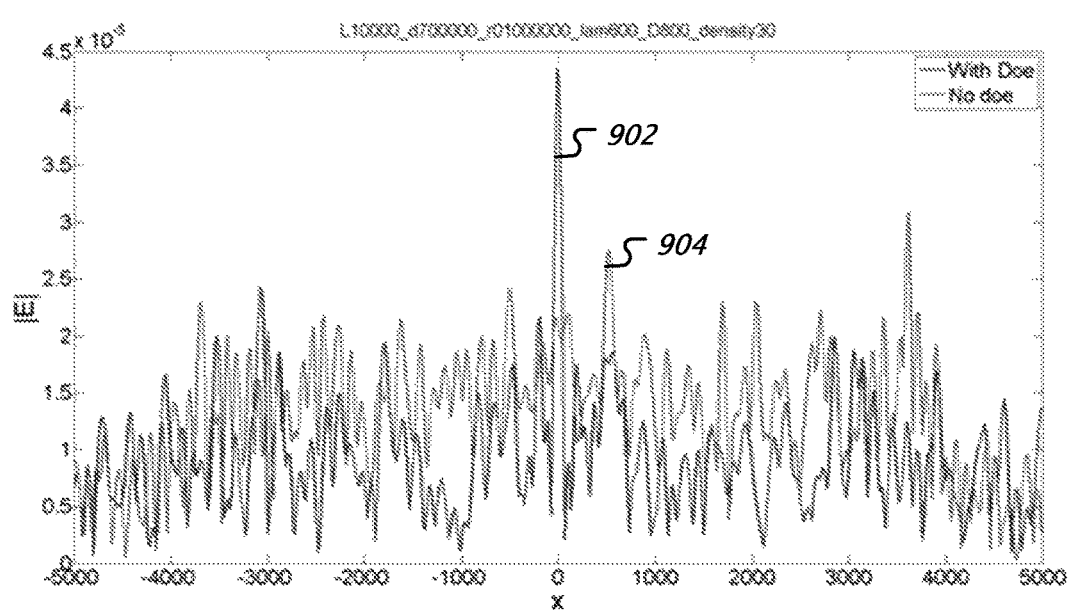
Figure 10:
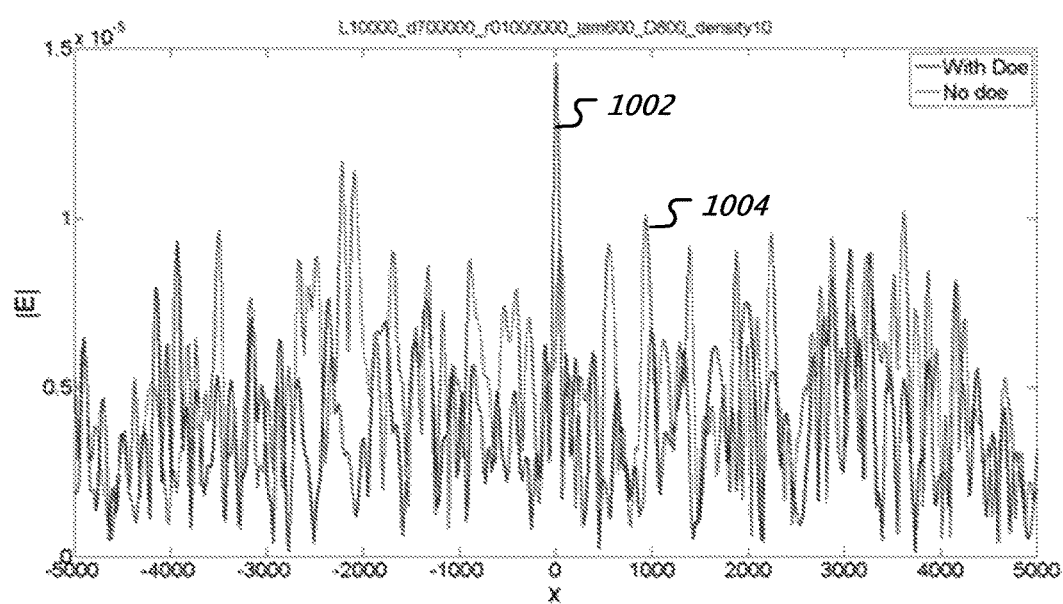
Figure 11:
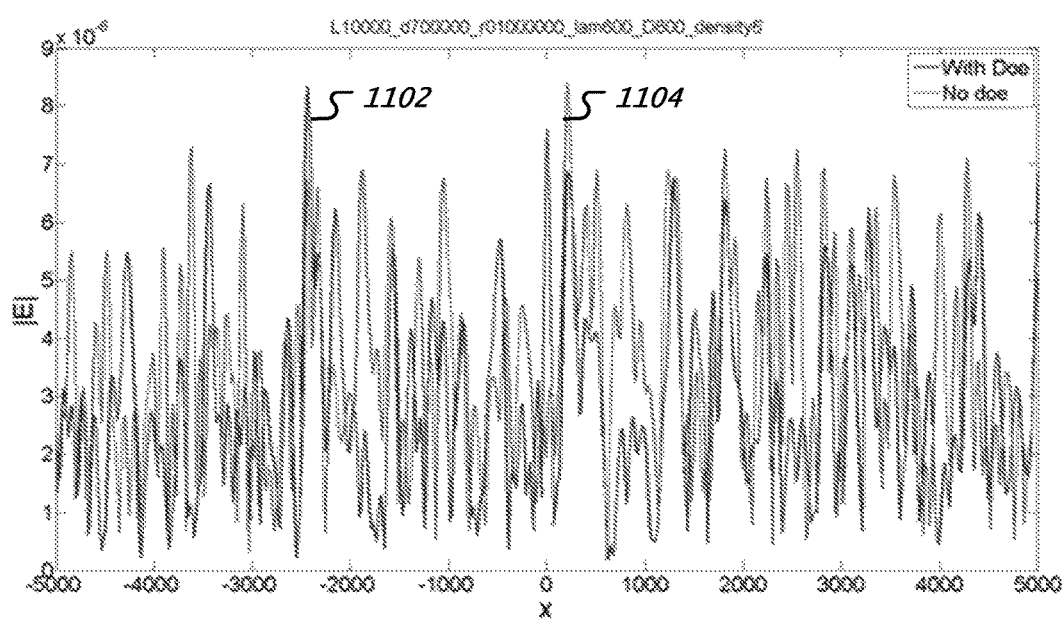
FIG. 11 shows a plot of an electric field magnitude of the back scattering of aerosol medium with area density 6/mm². No back scattered focusing is also shown of the case without projected zone plate (labeled as 'no DOE' 1104).
Figure 12:
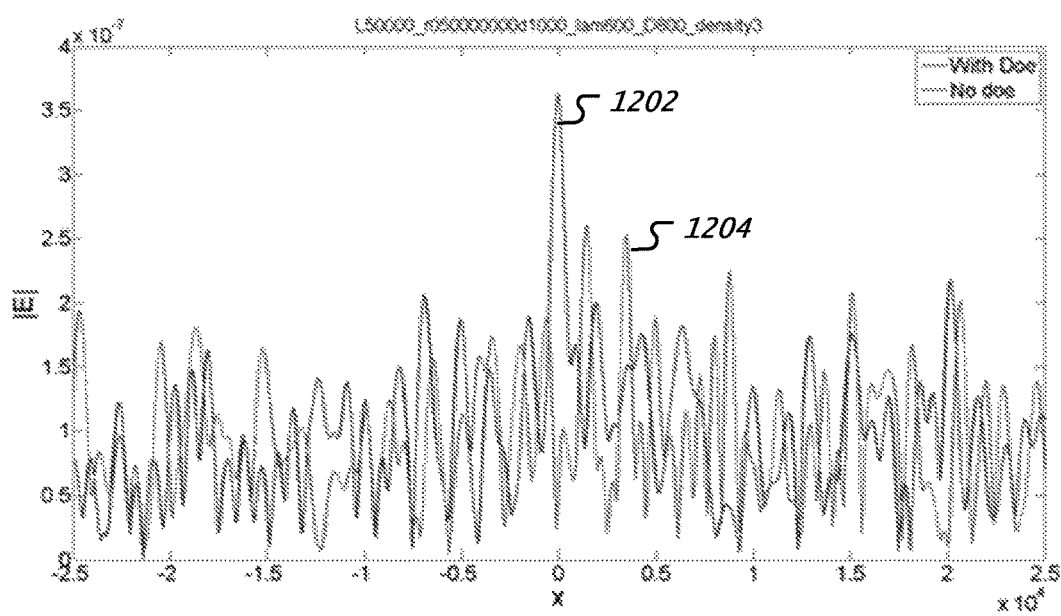
FIG. 12 shows a plot of an electric field magnitude of the back scattering of aerosol medium with area density 3/mm² (curve 1202). No back scattered focusing is also shown of the case without projected zone plate (labeled as 'no DOE' 1204).
Figure 16:
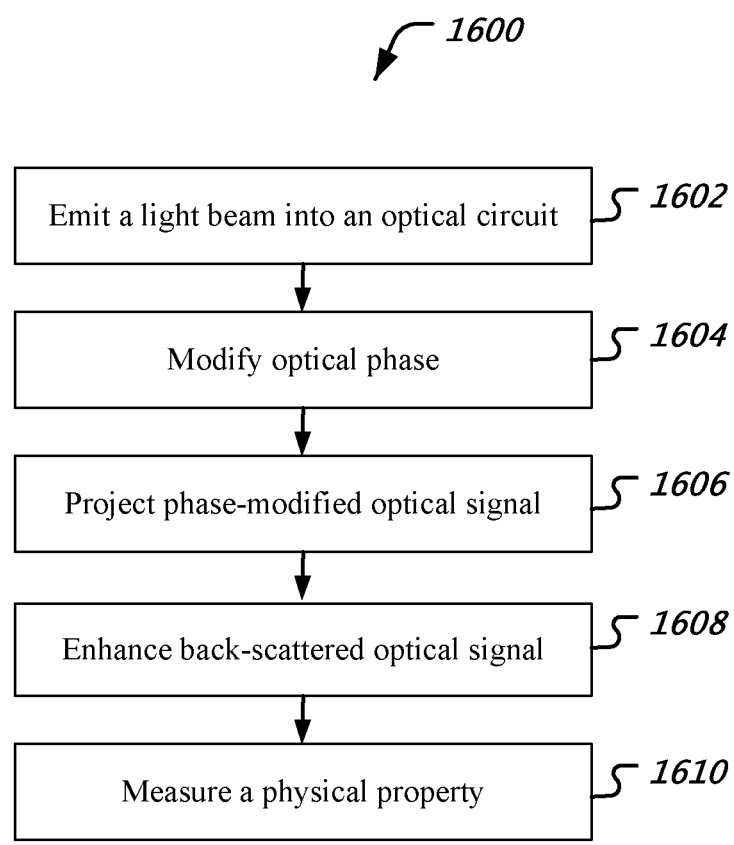

FIG. 16 shows an example flowchart for method 1600 for characterizing particulates in an aerosol medium, according to some embodiments. At 1602, a light beam is emitted into an optical circuit to split the light beam into a signal beam and a reference beam. At 1604, the optical phase of the signal beam is modified by a spatial light modulator including a zone plate of the optical circuit to form a phase-modified optical signal. At 1606, the phase-modified optical signal is projected by a lens into an aerosol medium to form a an optical field distribution pattern. The projected optical field distribution pattern illuminates the aerosol medium in a way that causes the back scattered light to constructively add together in phase or interfere forming an enhanced back scattered signal that includes a concentrated optical spot at an optical detector. At 1608, the enhanced back scattered signal is amplified using a mechanism such as a homodyne or a heterodyne detection scheme by interfering the back scattered light with the reference beam at the optical detector. At 1610, a physical property of particles in the aerosol medium is measured based on the detected back scattered light. The measurement may be performed using a detector and/or a processor. For example, additional implementation details and alternatives for implementing method 1600 are disclosed in the present patent document and described with respect to FIG. 1A, FIG. 1B and FIG. 14.

In some embodiments, an apparatus for characterizing particulates in an aerosol medium includes a light source that emits a light beam into an optical circuit to split the light beam into a signal beam and a reference beam, a spatial light modulator that modifies the optical phase of the signal beam to form a phase-modified optical signal, a lens positioned to project the phase-modified optical signal into an aerosol medium to form a an optical field distribution pattern, wherein the projected optical field distribution pattern illuminates the aerosol medium such that back scattered light constructively add together in phase or interfere forming an enhanced back scattered signal that includes a concentrated optical spot at an optical detector, the optical detector that amplifies the enhanced back scattered signal by interfering the back scattered light with the reference beam at the optical detector, and a measurement device that measures a physical property of particles in the aerosol medium based on the detected back scattered light. Various embodiments of the apparatus are described in the present document, including the description associated with FIG. 1A, FIG. 1B and FIG. 14.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A method for characterizing particulates in an aerosol medium, comprising:
    emitting a light beam into an optical circuit to split the light beam into a signal beam and a reference beam;
    modifying the optical phase of the signal beam by a spatial light modulator including a zone plate of the optical circuit to form a phase-modified optical signal;
    projecting the phase-modified optical signal by a lens into an aerosol medium to form a zone plate like optical field distribution pattern in the aerosol medium to cause the zone plate like optical field distribution pattern to form backscattered focusing outside the aerosol medium, wherein the projected zone plate like optical field distribution pattern illuminates the aerosol medium such that back scattered light constructively add together in phase or interfere forming an enhanced back scattered signal that includes a concentrated optical spot at an optical detector;

amplifying the enhanced back scattered signal by homodyne or heterodyne detection by interfering the back scattered light with the reference beam at the optical detector; and measuring a physical property of particles in the aerosol medium based on the detected back scattered light.

2. The method of claim 1, wherein the physical property includes a density or a size distribution of particles in the aerosol medium.

3. The method of claim 1, further comprising adjusting the optical field distribution pattern to form backscattered focusing for different sizes of the particles in the aerosol medium; and detecting size distribution of the particles in the aerosol medium.

4. The method of claim 1, further comprising:
using forward scattering signals caused by the particles in the optical field distribution pattern formed from the projecting the phase-modified optical signal; and
evaluating size and size distributions of the particles in the aerosol medium.

5. The method of claim 4, wherein the evaluating size distribution is performed by modifying a size of the zone plate.

6. The apparatus of claim 4, further including additional zone plates of different sizes for evaluating size distribution.

7. An apparatus for characterizing particulates in an aerosol medium, comprising:

a light source that emits a light beam into an optical circuit to split the light beam into a signal beam and a reference beam;

a spatial light modulator that modifies the optical phase of the signal beam to form a phase-modified optical signal;

a lens positioned to project the phase-modified optical signal into an aerosol medium to form a zone plate like optical field distribution pattern in the aerosol medium to cause the zone plate like optical field distribution pattern to form backscattered focusing outside the aerosol, wherein the projected zone plate like optical field distribution pattern illuminates the aerosol medium such that back scattered light constructively add together in phase or interfere forming an enhanced back scattered signal that includes a concentrated optical spot at an optical detector;

the optical detector that amplifies the enhanced back scattered signal by interfering the back scattered light with the reference beam at the optical detector; and a measurement device that measures a physical property of particles in the aerosol medium based on the detected back scattered light.

8. The apparatus of claim 7, wherein the physical property includes a density or a size distribution of particles in the aerosol medium.

9. The apparatus of claim 7, wherein the apparatus further uses forward scattering signals caused by the particles in the optical field distribution pattern formed from the projecting the phase-modified optical signal, and evaluates size and size distributions of the particles in the aerosol medium.

10. The apparatus of claim 7, wherein the spatial light modulator includes a zone plate of the optical circuit.

11. The apparatus of claim 7, wherein the signal detector performs detection using a homodyne or a heterodyne detection scheme.

* * * * *